United States Patent [19]

Tsai, Ying C. et al.

[11] Patent Number: 5,194,383
[45] Date of Patent: Mar. 16, 1993

[54] PROCESS FOR MAKING L-AMINOACYLASE

[75] Inventors: Tsai, Ying C.; Hsiang L. Hu; Yunn B. Yang, all of Taipei, Taiwan

[73] Assignee: National Science Council of Republic of China, Taipei, Taiwan

[21] Appl. No.: 795,504

[22] Filed: Nov. 21, 1991

[51] Int. Cl.$^5$ .......................... C12N 9/84; C12N 9/48; C12N 9/78; C12R 1/05
[52] U.S. Cl. .................................. 435/230; 435/71.2; 435/212; 435/219; 435/227; 435/233; 435/252.1; 435/829
[58] Field of Search ............... 435/230, 212, 219, 227, 435/233, 829, 71.2, 252.1, 230

[56] References Cited

U.S. PATENT DOCUMENTS 4,981,799  1/1991  Takahashi et al. .................. 435/233

FOREIGN PATENT DOCUMENTS 1-005488  1/1989  Japan .................................. 435/829

OTHER PUBLICATIONS

Tosa et al., Agr. Biol. Chem., vol. 33, 1047–1052 (1969).
Tosa et al., Agri. Biol. Chem., vol. 33, 1052–1059 (1969).

*Primary Examiner*—Herbert J. Lilling
*Attorney, Agent, or Firm*—Jacobson, Price, Holman & Stern

[57] ABSTRACT

A process for making L-aminoacylase includes a cultivation of microorganism selected from a specy of Alcaligenes, especially the *Alcaligenes denitrificans* DA 181, and a separation of a produced L-aminoacylase from the bacterial cells for obtaining the L-aminoacylase which may be further purified for the production of L-amino acid. The acylase made by such a process may have an increased stability, beneficial for its commercial and medical values.

3 Claims, 5 Drawing Sheets

PROCESS FOR MAKING L-AMINOACYLASE

BACKGROUND OF THE INVENTION

Chibata et al. early disclosed a method for producing L-aminoacylase by Aspergillus, which had been applied for industrial mass production [T. Tosa, T. Mori and I. Chibata, Agric. Biol. Chem., 33; 1047-1059 (1969)].

Such a conventional enzyme is composed of at least two subunits, with an optimum pH value of 8.0, and having a 2.5-fold enzyme activation as effected by cobalt ions, which however shows poor specific activity and shows no satisfactory stability, especially for thermal stability.

It is therefore expected to invent a process for making L-aminoacylase by microorganism for improving an activity, stability and other properties of a L-aminoacylase.

SUMMARY OF THE INVENTION

The object of the present invention is to provide a process for making L-aminoacylase including a cultivation of microorganism selected from species of Alcaligenes, especially the *Alcaligenes denitrificans* DA 181, and a separation of a produced L-aminoacylase from the bacterial cells for obtaining the L-aminoacylase which may be used for the production of L-amino acid. The acylase made by such a process may have an increased stability, beneficial for its commercial and medical values.

BRIEF DESCRIPTION OF THE DRAWINGS

FIG. 1 shows a SDS-polyacrylamide gel electrophoresis of L-aminoacylase of the present invention.

DETAILED DESCRIPTION

Figure 2:
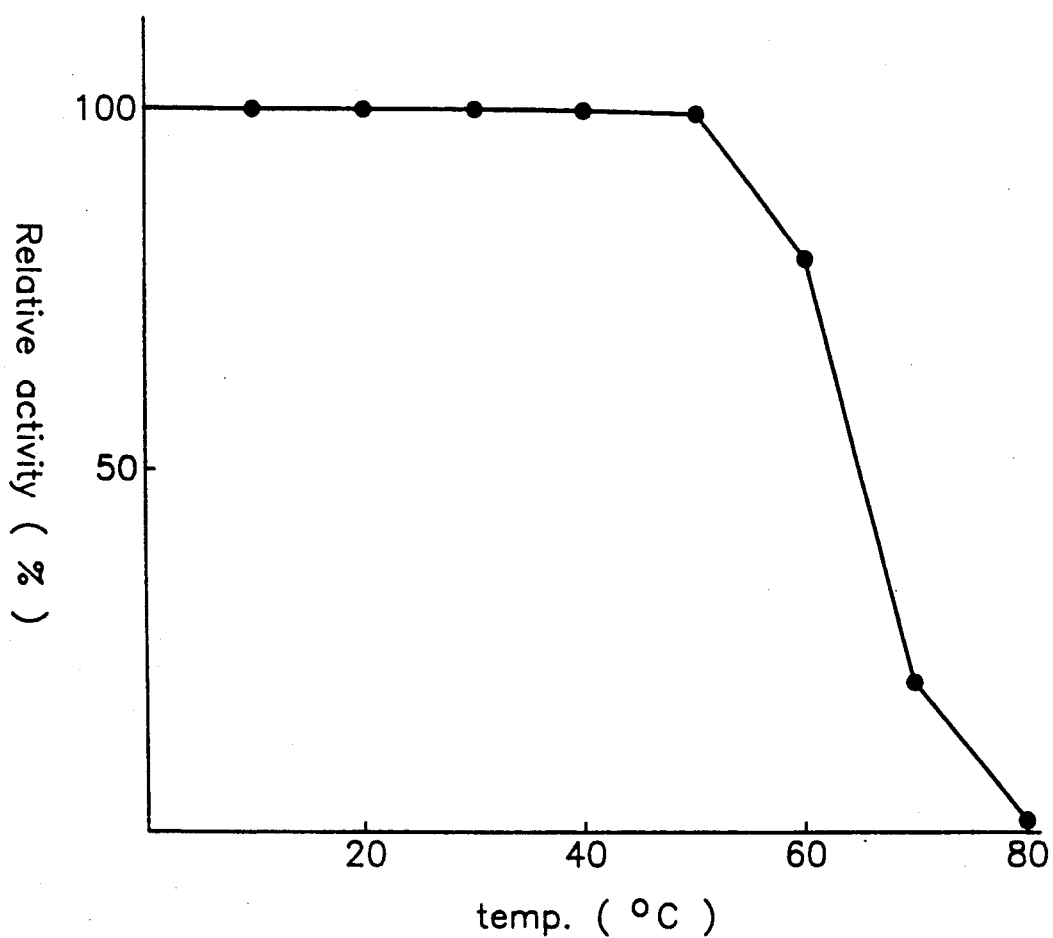
FIG. 2 shows a thermal stability of L-aminoacylase of the present invention.

The *Alcaligenes denitrificans* subsp. denitrificans DA181 of this invention is isolated from soil. The soil collected is prepared as a suspension liquid which is coated on a screened agar culture medium comprised of: 1% (W/V) N-acetyl-DL-methionine (or N-acetyl-DL-valine), 0.1% $K_2HPO_4$, 0.05% $MgSO_4.7H_2O$ and 1.5% agar (pH 7.0).

Strains able to grow on this medium are selected and cultivated in a liquid culture medium with constant shaking for 20 hours, containing the following composition: 1% N-acetyl-DL-methionine or N-acetyl-DL-valine, 0.5% yeast extract, 0.1% $K_2HPO_4$, and 0.05% $MgSO_4.7H_2O$ (pH 7.0).

The cells after being cultivated are collected and measured for obtaining their activities of L-aminoacylase.

Among the strains (more than ten strains) isolated from the soil capable of producing L-aminoacylase and D-aminoacylase, the DA181 strain is identified to be *Alcaligenes denitrificans* which is used for producing L-aminoacylase and has the following properties as shown in Table 1:

TABLE 1

|  | DA181 | DA1 |
|---|---|---|
| Form | coccal rods | coccal rods |
| Size (μm) | 0.6–0.9 × 0.8–2.0 | 0.5–1.0 × 0.6–2.0 |
| Gram stain | – | – |
| Catalase production | + | + |
| Spore formation | – | – |
| Motility | + | + |
| Lecithinase production | – | – |
| Cytochrome oxidase production | + | + |
| KCN growth | – | + |
| Growth anaerobically | – | – |
| Ammonium salt sugars acid from: | | |
| glucose | – | – |
| lactose | – | – |
| sucrose | – | – |
| mannitol | – | – |
| arabiose | – | – |
| xylose | – | – |
| Growth temperature (°C.) | 9–40 | 8–42 |
| Indole production | – | – |
| V-P reaction | – | – |
| Nitrate reduction | + | + |
| Denitrification | + | – |
| Gelatin liquefaction | – | – |
| Esculin hydrolysis | – | – |
| Urease | – | – |

*Alcaligenes denitrificans* DA181 was deposited on Feb. 25, 1992 at the Fermentation Research Institute, 1-3, Higashi 1-chome, Taukuba-shi, Ibaraki-Ken 305, Japan and is identified as No. FERM P-12045.

The preparation and purification of L-aminoacylase by using DA181 strain in accordance with the present invention is described in detail as follows:

A. The measurement of enzyme activity:

By using N-acetyl-L-alanine to be a substrate, an enzyme of suitable amount is dissolved in 50 mM Tris HCl buffer (pH 7.8) containing 15 mM N-acetyl-L-alanine for performing a reaction. After conducting the reaction at 37° C. for 10 minutes, a TCA solution is added for terminating the reaction. The L-alanine obtained in the reaction is measured by ninhydrin method. An enzyme activity unit defined herewith is a quantity of enzyme required for producing 1 μmole of L-alanine from 15 mM N-acetyl-L-alanine solution per minute.

B. The preparation and purification of enzyme:

Since the enzyme of the present invention is a constitutive enzyme, there is no need to additionally add inductive agent in the culture medium. Any culture medium suitable for growing the Alcaligenes may be used in this invention. The preferable nitrogen source is selected from: yeast extract, peptone, meat extract, and soymeal. The carbon source is preferably selected from organic acid, and the inorganic salts are preferably selected from: $K_2HPO_4$, $MgSO_4$, and NaCl. A liquid cultivation is preferred in this invention.

Two typical culture mediums are shown as follows:

| 1. First culture medium: | |
|---|---|
| N-acetyl-DL-leucine | 1% |
| yeast extract | 0.5% |
| peptone | 0.5% |
| $K_2HPO_4$ | 0.1% |
| $MgSO_4.7H_2O$ | 0.05% |
| | pH 7.80 |
| 2. Second culture medium: | |
| Acetyl salt | 1% |
| yeast extract | 3% |
| peptone | 0.5% |

| | |
|---|---|
| K₂HPO₄ | 0.1% |
| MgSO₄.7H₂O | 0.05% |
| | pH 7.80 |

The cultivation may be performed in a jar fermentor under air-penetrable agitation at about 30° C., pH 7.8, for 20-25 hours for reaching a highest enzyme activity. The bacteria cells are extracted, collected and stricken or broken by ultrasonic waves. The cell debris are removed by centrifugation. The supernatant is further purified by any purification methods, such as: ammonium sulfate fractionation, solvent precipitation, and chromatographies to obtain L-aminoacylase.

EXAMPLE

In a 5-liters jar fermentor, 3 liters of culturing medium containing 1% N-acetyl-DL-leucine, 0.5% yeast extract, 0.5% peptone, 0.1% K₂HPO₄ and 0.05% MgSO₄.7H₂O having a pH of 7.8 is fed, and the *Alcaligenes denitrificans* bacteria are incubated into the fermentor for bacterial growth and enzyme production of the present invention. The agitation speed is maintained at 250 rpm with air flowing rate of 3.0 vvm. After performing the cultivation at 30° C. for 25 hours, it is centrifuged for obtaining the cells, which are then broken. The cell debris are centrifuged and removed. The supernatant layer is then salted out to obtain protein crude product by adding 40% ammonium sulfate solution. The precipitated protein crude product is then dissolved in 100 ml 50 mM Tris-HCl buffer having a pH of 7.8 (buffer A) and dialyzed against the same buffer A to remove the ammonium sulfate salt.

The enzyme fraction is then applied to a Fractogel TSK DEAE 650 (s) column (2.5×70 cm) and the column is eluted with 1400 ml of buffer A at a flow rate of 60 ml/hr, then washed with 1700 ml of buffer A containing 60 mM NaCl, and subsequently eluted with 2000 ml of buffer A having 63 mM NaCl for isolating the L-aminoacylase.

The active enzyme fraction is collected, added with ammonium sulfate to have a 0.7M concentration and applied to TSK butyl-TOYOPEARL 650 (M) column (1.5×3 cm), which is washed with 10 ml buffer A containing 0.7M ammonium sulfate, and is eluted with linear gradient of 0.5 to 0.7M ammonium sulfate in buffer A. From which, the active enzyme fraction is collected, added with ammonium sulfate to a 1M concentration and is further applied to TSK Phenyl-TOYOPEARL 650 (M) column (1.2×3 cm), which is then washed with 30 ml of buffer A containing 0.6M ammonium sulfate, subsequently washed with 0.5M ammonium sulfate in buffer A (20 ml), and finally washed with 50 ml of buffer A having 0.45M ammonium sulfate to obtain purified L-aminoacylase having a specific activity of 696.7 units/mg. Table 2 shows the result produced and purified by the process as shown in the aforementioned example.

By performing only two step purification such as by ammonium sulfate and DEAE Chromatography, the partially purified enzyme of the present invention will exert a specific activity of 11.1 U/mg. Comparatively, the Chibata's Aspergillus enzyme may only have an activity of 37.2 μmoles/hr/mg after being purified by ammonium sulfate and acetone, which is equal to 0.6 U/mg, and is smaller than the activity of the enzyme of the present invention.

*Note: The above-mentioned activity data of Aspergillus enzyme is shown in a reference of "Studies on Continuous Enzyme Reactions." by T. Tosa, T. Mori, N. Fuse and I. *Chibata*, an investigation presented at the Annual Meeting of the Agricultural Chemical Society of Japan, Tokyo, Japan, Apr. 4, 1965.

TABLE 2

Summary of purification of L-aminoacylase

| steps | total volume (ml) | total protein (mg) | total activity (unit) | specific activity (U/mg) | recovery (%) | purification fold |
|---|---|---|---|---|---|---|
| crude | 100 | 2145 | 565.3 | 0.26 | 0.26 | 1 |
| (NH₄)₂SO₄ ppt. | 120 | 984 | 508.8 | 0.60 | 90 | 1.3 |
| TSK DEAE-650 (S) | 500 | 23 | 252 | 11.1 | 45 | 42.7 |
| TSK phenyl 650 (M) | 20 | 0.351 | 172.3 | 490.8 | 31 | 1885 |
| TSK butyl 650 (M) | 25 | 0.121 | 84.3 | 696.7 | 15 | 2679.5 |

The several properties of L-aminoacylase of the present invention are described hereinafter:

1. Molecular weight

Figure 1:
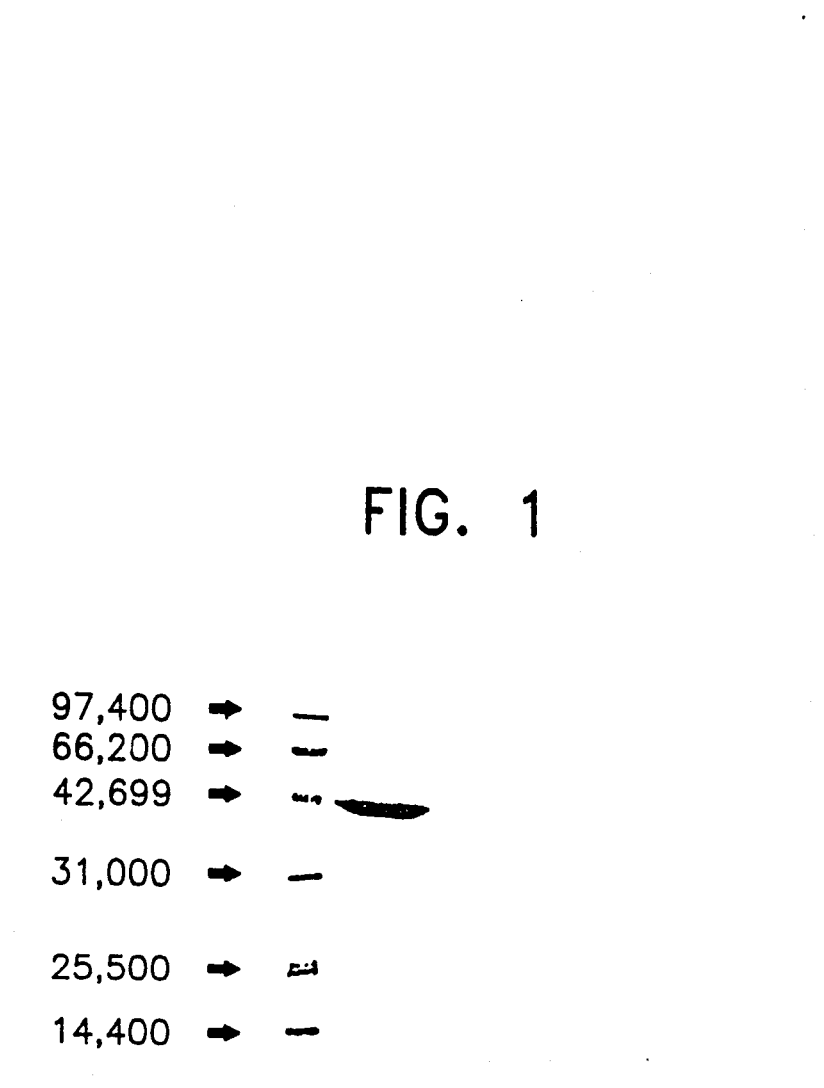

The molecular weight of L-aminoacylase of the present invention is 80,000 which is measured by Gel filtration method by using HPLC column G 3,000 SW; and another molecular weight is 40,000 (FIG. 1) when measured by 12% SDS-PAGE method, indicating that the enzyme of this invention is comprised of two subunits.

2. Isoelectric point

The $p^I$ value of isoelectric point of the acylase of the present invention is 5.1 which is measured by polyacrylamide gel isoelectrofocusing.

3. Effect and substrate specificity

This enzyme may hydrolyze N-acetyl-L-amino acids with a higher reactivity, but hydrolyze the N-acetyl-D-amino acids with a lower reactivity. The reactivity with the N-chloroacetyl-L-valine is especially high.

A comparison of the substrate specificity of L-amino acylase of this invention with D-amino acylase is summarized as shown in Table 3.

TABLE 3

Comparison on the substrate specificity of L-amino acylase and D-amino acylase.

| | Relative activity (%) | | |
|---|---|---|---|
| | L-amino acylase | | D-amino acylase |
| Substrate | L-form | D-form | D-form |
| N-chloroacetyl-valine | 100 | 0.8 | 66 |
| N-acetyl-valine | 95 | 7 | 6 |
| N-acetyl-alanine | 78 | 0 | 25 |
| N-acetyl-tyrosine | 36 | ND | ND |
| N-acetyl-phenylalanine | 34 | 0.9 | 81 |
| N-acetyl-methionine | 30 | 0.12 | 100 |
| N-acetyl-tryptophan | 11 | 0.9 | 33 |
| N-acetyl-leucine | 10 | 2 | 60 |
| N-acetyl-asparagine | 3 | 0 | 17 |
| N-acetyl-aspartic acid | 1 | ND | ND |
| N-acetyl-glutamic acid | 0.12 | ND | ND |
| N-acetyl-histidine | 0.08 | ND | ND |
| N-acetyl-arginine | 0.04 | ND | ND |
| N-acetyl-alloisoleucine | ND | 0 | 12 |
| N-acetyl-phenylglycine | ND | 0 | 5 |

*ND: not determined
The enzyme activity was determined at 37° C. in 50 mM Tris-CHl buffer pH 8.0 by ninhydrin method.

4. Thermal stability

The enzyme is dissolved in buffer A and is kept for one hour at each different temperature to test a remaining or residual activity of the enzyme to obtain the result as shown in FIG. 2. From the test, this enzyme is quite stable below 50° C. and may still remain 80% activity at 60° C. after one hour. However, Chibata's Aspergillus enzyme may only have about 50% activity at 65° C. after 15 minutes, which is less than the activity of this invention, with only a small temperature difference of 5° C. from this invention. Accordingly, this invention may have a better thermal stability than that of the prior art.

5. pH stability

Figure 3:
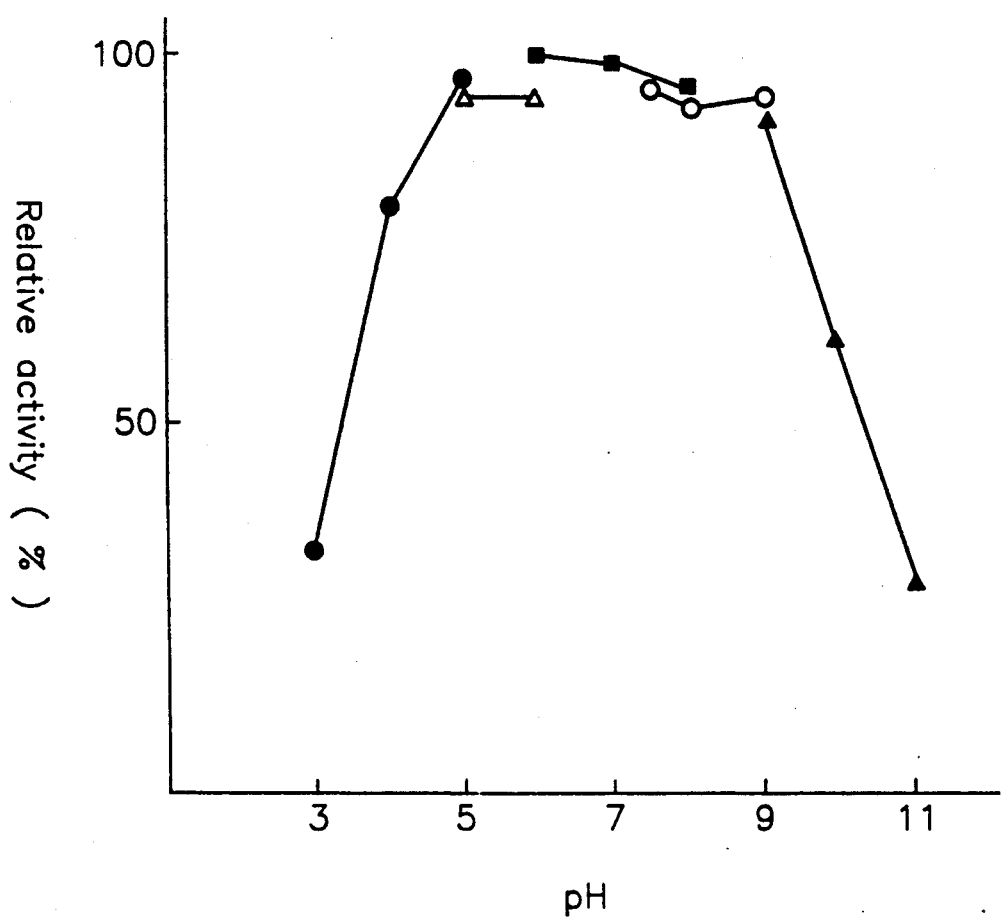
FIG. 3 shows a pH stability of L-aminoacylase.

The enzyme is dissolved in buffers of different pH values and is kept for one hour at 37° C. Then, the pH value is adjusted to 7.5 by using 0.5M HEPES buffer of pH 7.5. The remaining activity of the enzyme is summarized in FIG. 3. From the test, this enzyme is very stable at pH value ranging 5 to 9.

6. Optimum reaction temperature

Figure 4:
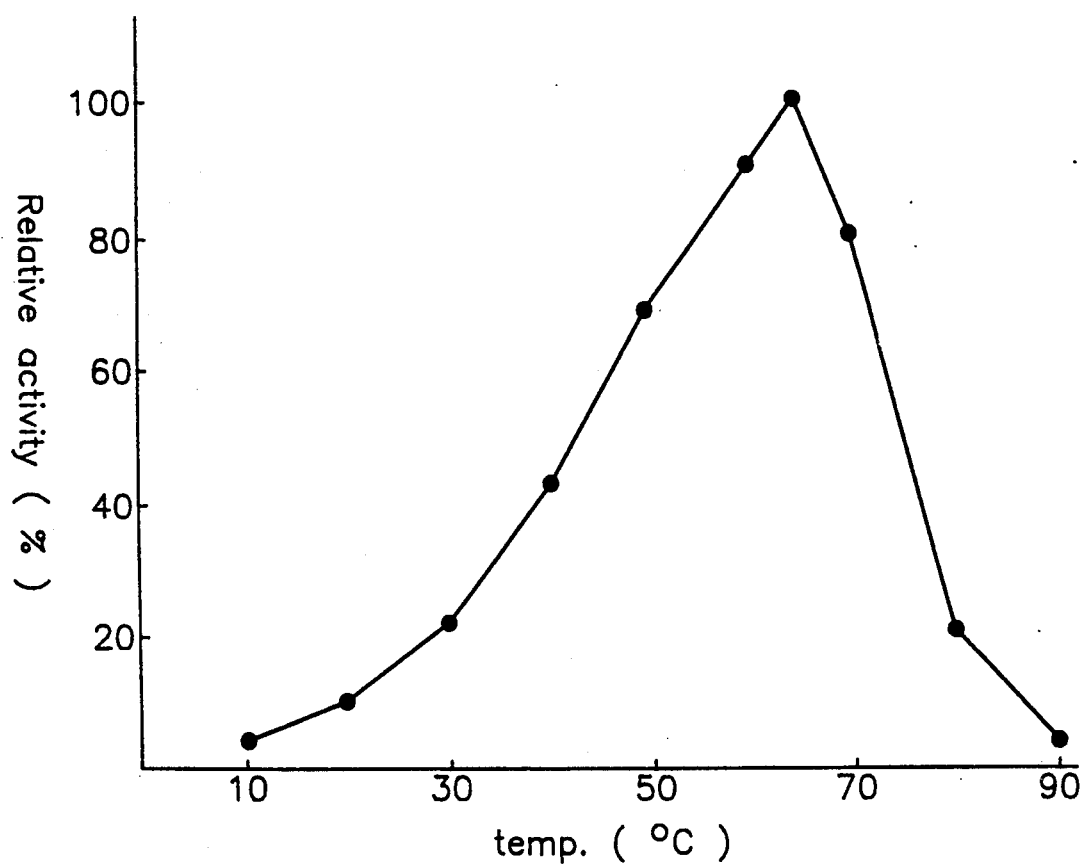
FIG. 4 shows an effect of temperature on the L-aminoacylase.

This enzyme is dissolved in buffer A to test its activity at different temperatures by ninhydrin method to obtain the results as shown in FIG. 4. The optimum reaction temperature of the present invention ranges from 60° to 70° C.

7. Optimum reaction pH value

Figure 5:
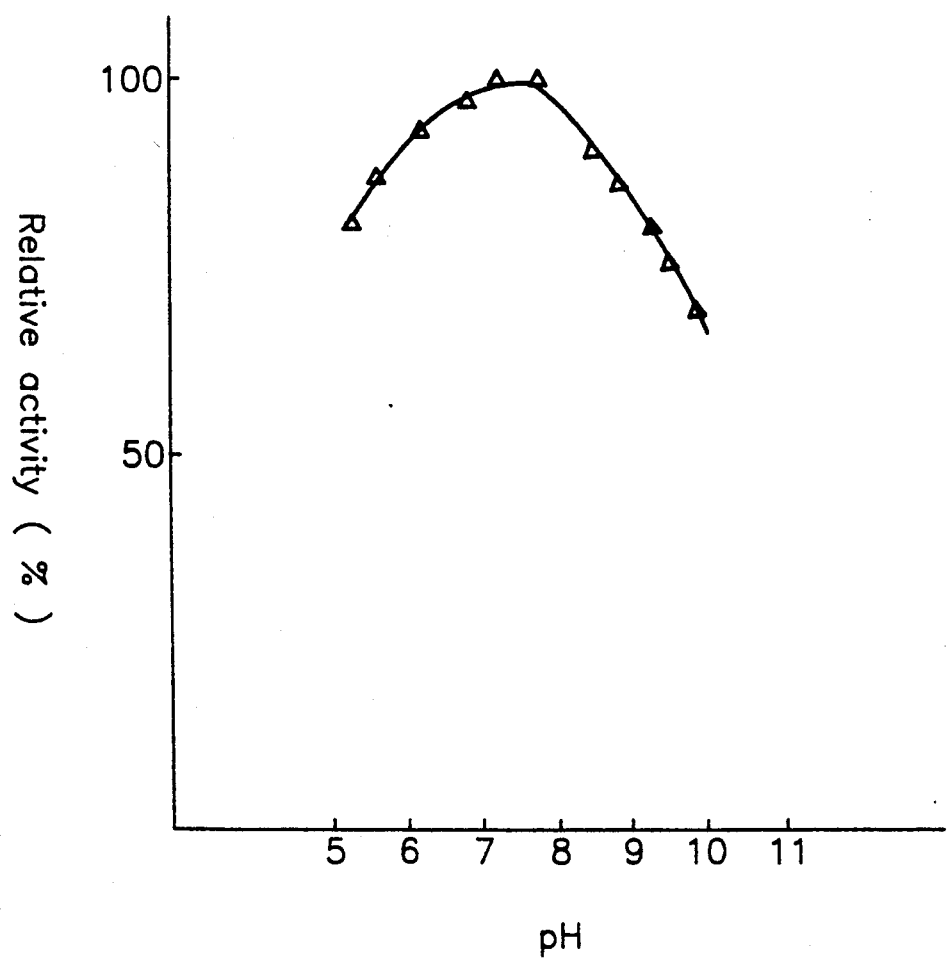
FIG. 5 shows an effect of pH on the activity of L-aminoacylase of the present invention.

The enzyme of this invention is dissolved in buffers of different pH values to test its activities at 37° C. by ninhydrin method. The testing result is shown in FIG. 5, from which, an optimum reaction pH value is about 8.0.

8. Influence by metallic ions

By dissolving the enzyme of the present invention in buffers (buffer A) each containing different ion of 1 mM concentration, a remaining activity in each buffer is measured by ninhydrin method after 30 minutes at 37° C. to obtain the testing result as shown in Table 3, from which, the enzyme of this invention is inhibited by ions of $Cd^{++}$, $Zn^{++}$, $Pb^{++}$, $Fe^{++}$, $Cu^{++}$ an $Hg^{++}$.

The present invention discloses a process for making L-aminoacylase by culturing *Alcaligenes denitrificans* DA181 by a liquid cultivation method. The L-aminoacylase may be used for producing L-amino acids.

TABLE 4

| Effect of various metal ions on L-amino acylase activity | | |
|---|---|---|
| metal ion | concentration (mM) | relative activity of L-amino acylase (%) |
| None | 1 | 100 |
| $MgCl_2$ | 1 | 98 |
| $CoCl_2$ | 1 | 120 |
| $NiCl_2$ | 1 | 95 |

TABLE 4-continued

| Effect of various metal ions on L-amino acylase activity | | |
|---|---|---|
| metal ion | concentration (mM) | relative activity of L-amino acylase (%) |
| $BaCl_2$ | 1 | 92 |
| $SrCl_2$ | 1 | 80 |
| $CaCl_2$ | 1 | 94 |
| $MnCl_2$ | 1 | 86 |
| $CdCl_2$ | 1 | 16 |
| $ZnCl_2$ | 1 | 61 |
| $FeCl_2$ | 1 | 15 |
| $PbCl_2$ | 1 | 50 |
| | $10^{-1}$ | 71 |
| | $10^{-2}$ | 71 |
| | $10^{-3}$ | 97 |
| $CuCl_2$ | 1 | 5 |
| | $10^{-1}$ | 77 |
| | $10^{-2}$ | 90 |
| | $10^{-3}$ | 94 |
| $HgCl_2$ | $10^{-3}$ | 0 |
| | $10^{-4}$ | 0 |
| $EDTA.2Na$ | 1 | 55 |

Various metal ions were incubated with an appropriate amount of enzyme for 30 min in 50 mM Tris-HCl pH 8.0. The remaining activity was determined by ninhydrin method.

We claim:

1. A process for making L-aminoacylase comprising: culturing *Alcaligenes denitrificans* DA181 in a culturing medium for growing cells for forming L-aminoacylase enzyme; and isolating said L-aminoacylase enzyme from the cells of the culturing medium.

2. A process for making L-aminoacylase comprising: culturing *Alcaligenes denitrificans* strain DA181 in a culturing medium by a liquid cultivation method for growing cells for forming an enzyme of L-aminoacylase, and isolating, and purifying said L-aminoacylase from said cells and said culturing medium, said L-aminoacylase having a plurality of properties including: a substrate specificity capable of hydrolyzing N-acyl-L-amino acids and unable for hydrolyzing N-acyl-D-amino acids, having a molecular weight of 80,000 measured by gel filtration method and 40,000 by SDS-PAGE method, having an isoelectric point of 5.1, a thermal stability of 80% of remaining activity at 60° C. for one hour and a pH stability at pH value of 5-9, an optimum reaction temperature of 60°-70° C. and optimum reaction pH value of 8.0, and being inhibited by lead, zinc, ferrous, cupric, and mecuric ions.

3. The process according to claim 2, wherein the *Alcaligenes denitrificans* DA181 is cultured in a liquid culturing medium containing an acetyl compound selected from the group consisting of N-acetyl-DL-leucine and acetyl salt under air-penetrable agitation at 30° C., pH 7.8 for 20 to 25 hours.

* * * * *